United States Patent [19]
Oh et al.

[11] Patent Number: 5,705,353
[45] Date of Patent: Jan. 6, 1998

[54] METHOD OF REDUCING INTERFERENCES IN ASSAYS

[75] Inventors: Chan S. Oh, Chino Hills; Julie S. Kim, Placentia; Anthony K. Cheng, Anaheim, all of Calif.

[73] Assignee: Beckman Instruments, Inc., Fullerton, Calif.

[21] Appl. No.: 483,288

[22] Filed: Jun. 7, 1995

[51] Int. Cl.$^6$ .................. G01N 33/53; G01N 33/537; G01N 33/543

[52] U.S. Cl. .................. 435/7.92; 435/174; 436/501

[58] Field of Search .................. 435/7.92, 174; 436/501

[56] References Cited

U.S. PATENT DOCUMENTS

| | | | |
|---|---|---|---|
| 4,649,105 | 3/1987 | Kasahara et al. | 435/5 |
| 4,788,138 | 11/1988 | Tung et al. | 435/5 |
| 4,806,311 | 2/1989 | Greenquist | 422/56 |
| 4,806,467 | 2/1989 | Porter et al. | 435/5 |
| 4,914,041 | 4/1990 | Thrasher | 436/509 |
| 4,918,001 | 4/1990 | Kolde | 435/24 |
| 4,923,439 | 5/1990 | Seidel et al. | 604/6 |
| 5,011,770 | 4/1991 | Kung et al. | 435/6 |
| 5,071,745 | 12/1991 | Triscott et al. | 435/7.4 |
| 5,168,057 | 12/1992 | Oh et al. | 435/174 |
| 5,196,351 | 3/1993 | Harris et al. | 436/501 |
| 5,278,081 | 1/1994 | Deger et al. | 436/518 |
| 5,422,281 | 6/1995 | Harris et al. | 436/501 |
| 5,460,948 | 10/1995 | Atkinson et al. | 435/25 |
| 5,476,771 | 12/1995 | Reid et al. | 435/13 |
| 5,534,620 | 7/1996 | Oh et al. | 530/413 |
| 5,580,746 | 12/1996 | You | 435/18 |

FOREIGN PATENT DOCUMENTS

WO 8706006  10/1987  WIPO.

OTHER PUBLICATIONS

Oh et al, Clinica Chimica Acta, vol 218(1) pp. 59–71, 1993.

Price, C P et al, Principles and Pract. of Immunoassay, 1993, pp. 446–481.

Kuemmerle, S.C. et al, Clin. Chem vol.38(10) pp. 2073–2077, 1992.

Oh et al, J. Pharm. & Biomed. Analysis, vol 10(10–12), pp. 813–819 1992.

Ratcliff, J.G, Br. Med. Bull. 1974, pp. 32–37, vol. 30(1).

*Primary Examiner*—James C. Housel
*Assistant Examiner*—Ginny Allen Portner
*Attorney, Agent, or Firm*—William H. May; Margaret A. Kivinski; Sheldon & Mak

[57] ABSTRACT

An assay for determining the presence of an analyte of interest in a test sample containing an interfering substance that interferes with the assay is disclosed. The assay comprises the steps of forming a reaction mixture by combining in an assay medium (i) an assay system containing components for detecting the analyte of interest, (ii) a test sample containing the analyte and an interfering substance, and (iii) an additional amount of the interfering substance in a quantity sufficient to substantially mask the effect of the interfering substance in the test sample. This reaction mixture is incubated under conditions sufficient to allow complex formation. This resultant complex formation is detected and the presence of the analyte in the test sample is determined.

28 Claims, 4 Drawing Sheets

FIG. 1.
SERUM AND PLASMAS EFFECT OF HEPARIN IN A GENTAMICIN ASSAY WITHOUT HEPARIN IN ASSAY MEDIUM

Fig. 3.
ABSORBANCE SPECTRA OF A PHENYTOIN ASSAY WITH HEPARIN INCLUDED IN THE ASSAY BUFFER

FIG. 9.
ABSORBANCE SPECTRA OF A PHENYTOIN ASSAY WITH HEPARIN INCLUDED IN THE LATEX - AVIDIN BIDENTATE DILUENT

METHOD OF REDUCING INTERFERENCES IN ASSAYS

BACKGROUND

Diagnostic assays play a significant role in the detection and diagnosis of diseases. The development of diagnostic assay technology has made possible the precise measurement of minute amounts of analyte in samples of serum, plasma, saliva, cerebral spinal fluid, amniotic fluid and urine. Applications of assays include measuring drug concentrations administered to patients for the treatment of diseases and detecting blood components resulting from diseases including cancer. Thus, their applications in the fields of biology and medicine have made them increasingly important and versatile as diagnostic tools.

There are complications, however, with the uses of assays. The sensitivity and accuracy of these assays are often limited by interfering substances present in the sample. Such interfering substances can make detection and measurement of the analyte of interest unreliable, as well as decrease the sensitivity of the assay.

The effects of interfering substances can be disastrous since their presence in assays could cause inaccurate results leading to misdiagnosis and potentially inappropriate treatment. Interfering substances can be exogenous or endogenous. Exogenous interferences are defined as any interfering substance caused by the addition of external factors in vivo or in vitro. Examples include, the introduction of interfering substances by sample storage, tubes, and radioactive contamination. Endogenous interference can be caused by factors which exist in the patents' blood in physiological or pathophysiological conditions. Examples of endogenous interferences can include rheumatoid factors, hyperlipidemia and complement.

There are a variety of known methods for reducing the effect of interfering substances in assays. One approach is to dilute the test samples to attenuate the effects of the interfering substance. However, this method is not ideal because it simultaneously decreases the sensitivity of the assay.

An alternative method is to extract the test samples. However, this approach disadvantageously requires a supplemental step which can introduce an additional source of errors.

Other methods for reducing the effects of interfering substances involve rigorous pre-treatment of the test sample by exposing the test sample to heat, enzymes or reducing/oxidative reagents. The disadvantages associated with these methods is that the pre-treatment can alter the test sample containing the analyte of interest.

Another method involves adding scavenging or neutralizing factors to the assay which are capable of inhibiting the effects of interfering substances. However, this method eliminates only some of the effects of these substances. Furthermore, a disadvantage associated with this method is sample variation resulting in an assay which is not standardized.

Therefore, while these procedures for reducing the effects of interfering substances can be useful, they are disadvantageously time consuming and they have the undesirable effect of drastically reducing the potential sensitivity and accuracy of the assay as a result of the required manipulations.

Heparin is a typical interfering substance found in plasma and lipemia test samples. Heparin interference is often due to the sodium and lithium heparin tubes used to collect the samples. For example, with regard to avidin biotin bidentate conjugate drug assays, heparin interference leads to enhanced reaction rate and low drug concentration measurements. This interference is believed to be associated with the interaction between positively charged avidin and negatively charged heparin. Previous attempts to remove heparin interference from bidentate conjugate drug assays were either partially or totally ineffective and were found to be assay dependent.

For the foregoing reasons, there is a need for a sensitive specific assay that can accurately determine the presence of an analyte in a sample with little or no effects from interfering substances. Further, it would be advantageous to have an assay which would be capable of satisfying the above criteria yet able to maintain the standardization of the assay by avoiding sample variation.

SUMMARY

The present invention is directed to an assay that meets these needs. The assay is used to determine the presence of an analyte of interest in a test sample where the test sample contains an interfering substance. The assay comprises the steps of forming a reaction mixture, by combining in an assay medium (i) an assay system comprising a first binding member, a second binding member, a spacer member intermediate between the members, a first binding partner and a second binding partner, (ii) a test sample containing the analyte and an interfering substance that is capable of interfering with the assay, and (iii) an additional amount of the interfering substance in a quantity sufficient to substantially completely mask the effect of the interfering substance in the test sample. The first binding member is capable of binding to the first binding partner, the first binding partner being capable of binding to the analyte. The second binding member is capable of binding to the second binding partner. The second binding partner can aid in detecting either bound or unbound analyte in the reaction mixture. The interfering substance can interfere with the assay by interacting with the second binding partner. This reaction mixture is incubated under conditions sufficient to allow the formation between the analyte and the binding partner. This resultant complex formation is detected and the presence of the analyte in the test sample is determined.

The reaction mixture can include a sufficient additional interfering substance where in the step of combining, substantially all of the second binding partners in the reaction mixture can be non-specifically bound to interfering substance.

The first and second binding members can be members of a bidentate compound. The first binding member can be at least one of the following: theophylline, carbamazepine, gentamicin, acetaminophen, phenytoin, and phenobarbital. The first binding partner which specifically binds to the analyte of interest can be antibody or an antibody fragment. The second binding member can be biotin and the second binding partner can be avidin.

The assay system can further comprise a third binding member, the third binding member capable of being attached to the spacer intermediate. The first, second and third binding members can be members of a tridentate compound.

The interfering substance of the assay can be heparin. The additional amount of heparin added to the reaction mixture is generally from about 20 units and 150 units. Preferably, the additional amount of heparin is from about 40 units to about 120 units. More preferably, the amount of heparin is from about 40 units to about 90 units.

This assay can be performed on test samples such as serum, plasma, saliva, cerebral spinal fluid, amniotic fluid, urine, feces, mucus, cell extracts, tissue extracts and pus.

The analyte of interest can be substantially any biological substance such as drugs, hormones, vitamins, enzymes, proteins, antibodies, polysaccharides, bacteria, protozoa, parasites, fungi, viruses, cell antigens, tissue antigens, blood cell substances and blood fluid substances.

When the analyte of interest is a drug, the drug can be theophylline, carbamazepine, gentamicin, acetaminophen, phenytoin, phenobarbital, digoxin, valproic acid, thyroxine, disopyramide, lidocaine, procainamide, propranolol, quinidine, amikacin, tobramycin, tricyclic antidepressants, ethosuximide, primidone, acetylsalicylic acid and methotrexate.

A test kit for detecting the presence of an analyte of interest in a test sample is also disclosed. The test sample can contain an interfering substance that is capable of interfering with the assay. The test kit comprises at least one container containing components which can be partially or completely pre-combined or uncombined. The components include, (i) an assay medium (ii) a first binding member capable of binding to a binding partner for the analyte (iii) the first binding partner capable of binding to the analyte (iv) a second binding member capable of binding to a second binding partner (v) the second binding partner aiding detection of either bound or unbound analyte in the reaction mixture, wherein the interfering substance in the test sample is capable of interfering with the assay by interacting with the second binding member and (vi) an additional amount of the interfering substance in a quantity sufficient to substantially completely mask the effect of the interfering substance in the test sample.

These and other features, aspects and advantages of the present invention will become better understood with reference to the following description and appended claims.

DESCRIPTION OF THE DRAWINGS

These and other features, aspects, and advantages of the present invention will become better understood with reference to the following description, appended claims, and accompanying drawings where:

DESCRIPTION

According to the present invention, there is provided an assay for detecting an analyte of interest in a test sample which includes an additional amount of interfering substance in the assay medium to substantially reduce or eliminate the effects of the interfering substance. Such an assay comprises the steps of forming a reaction mixture, incubating the reaction mixture and determining the presence of the analyte in the test sample.

I. FORMING THE REACTION MIXTURE

The reaction mixture is formed by combining in an assay medium an assay system, a test sample containing the analyte and an interfering substance and an additional amount of interfering substance.

A. The Assay System

The assay system comprises a first binding member, a second binding member, a spacer member intermediate between the members, a first binding partner and a second binding partner. The first binding member is capable of binding to the first binding partner and this first binding partner is capable of binding to the analyte. The second binding member is capable of binding to the second binding partner. The second binding partner can aid in detecting either bound or unbound analyte in the reaction mixture. In the combining step, the reaction mixture can include sufficient additional interfering substance where substantially all of the second binding partners in the reaction mixture are non-specifically bound to interfering substance.

The first and second binding members can be members of a bidentate compound. The assay system can further comprise a third binding member which is capable of binding to the spacer intermediate. When there are three binding members, they can be members of a tridentate compound.

1. The First Binding Member

The first binding member is typically a member of a bidentate compound and can be a member of a tridentate compound. The first bidentate member is selected to be identical or analogous to the analyte of interest which may be present in the test sample. What is preferred is that the first bidentate member be able to compete with free analyte for the same specific binding partner. The first binding member can be theophylline, carbamazepine, gentamicin, acetaminophen, phenytoin and phenobarbital.

The first binding member is capable of binding to a first binding partner. The first binding partner is capable of binding to the analyte. The first binding partner which specifically binds to the analyte of interest can be an antibody or an antibody fragment.

2. The Second Binding Member

The second binding member can also be a member of a bidentate compound and can be a member of a tridentate compound. The second binding member preferably can aid in detection of bound or unbound analyte in the reaction mixture by being capable of coupling to a system that can detect changes in reaction conditions due to the presence of the analyte of interest. For example, the second binding member is capable of specifically binding to a second binding partner. The second binding member preferably is biotin. When the second binding member is biotin, the second binding partner is typically avidin, streptavidin and other derivatives capable of binding to biotin. Such derivatives typically have small binding constants. The second binding partner is preferably avidin. Avidin-biotin bidentate conjugate systems can be employed to detect analytes of interest by forming complexes.

Optionally, when avidin is used, the avidin can be conjugated to latex, forming a latex-avidin conjugate. The presence of the latex-avidin conjugate can increase assay sensitivity, reduce the amount of antiserum used and substantially reduce or eliminate matrix problems.

A description of latex-avidin conjugate preparations is incorporated by reference (U.S. pending application 08/248, 479). Generally, macroscopic particles are employed which are preferably made of latex. The use of such macroscopic particles decreases the extent of complex formation needed to obtain a discernible change in light scatter or reflection for measurements. Because of the presence of macroscopic particles, complexes that could be otherwise too small to be detected can be readily measured. The presence of the particles affects both the rate of detectable complex formation, and the lower limit of analyte that can be detected.

The size of the latex particle can vary from less than 50 nm to more than 100 nm. In such assays, the use of 60 to 100 nm particles is preferred.

B. The Test Sample

The test sample preferably contains an analyte of interest and an interfering substance. The test sample can be any biological fluid including whole blood, serum or plasma, saliva, cerebral spinal fluid, amniotic fluid, urine, feces, mucus, cell or tissue extracts and pus.

The analyte of interest is a substance suspected of being in the test sample whose presence or concentration is to be determined. The analyte is a material that can include drugs, hormones, vitamins, enzymes, proteins, antibodies, polysaccharides, bacteria, protozoa, parasites, fungi, viruses, cell and tissue antigens, and other blood cell or blood fluid substances. According to this invention, the analyte of interest is preferably a drug selected from the group consisting of theophylline, carbamazepine, gentamicin, acetaminophen, phenytoin, phenobarbital, digoxin, valproic acid, thyroxine disopyramide, lidocaine, procainamide, propranolol, quinidine, amikacin, chloramphenicol, kanamycin, tobramycin, tricyclic antidepressants, ethosuximide, primidone, acetylsalicylic acid and methotrexate.

The interfering substance is a substance that can be present in the biological fluid. Typical interfering substances found in test samples are heparin, rheumatoid factors, salicylates, fibrinogen and Clq (a component of complement). Preferably, the interfering substance is heparin.

C. An Additional Amount of Interfering Substance

Forming the reaction mixture further includes an additional amount of the interfering substance in a quantity sufficient to at least partially mask the effect of the interfering substance in the test sample. In the step of combining, the reaction mixture preferably includes sufficient additional interfering substance that substantially all of the second binding partners in the reaction mixture are non-specifically bound to interfering substance. Preferably, this non-specific binding is a neutralization interaction.

The amount of interfering substance added to an assay to at least partially mask the effect of the interfering substance in the test sample, depends on the assay in question. This amount can be determined for each assay by routine trial and experiment. The precise optimum quantity should be checked.

The interfering substance is preferably heparin. When the interfering substance is heparin, the second binding partner is preferably avidin. Heparin interference can be associated with the interaction between the positively charged avidin (pI of 10) and the negatively charged heparin. This interaction can lead to enhanced reaction rate and low drug concentration. The introduction of an additional amount of heparin sufficient to neutralize the positively charged avidin can reduce substantially reduce or eliminate the effects due to heparin interference.

When heparin is the interfering substance, the additional amount of heparin added to the reaction mixture is generally between about 20 units and 150 units. At least 20 units is needed to substantially reduce the effects of heparin in the assay. Greater than 150 units may interfere with the assay. Preferably, the additional amount of heparin is between about 40 units to about 120 units. More preferably, the amount of heparin added is from about 40 units to about 90 units.

D. Two-Reagent and Three-Reagent Assay System

Various assay formulations and their applications for detecting and quantitating analytes of interest can be used. However, as described by Yan, C. et al. in "Reagents and Methods for the Rapid and Quantitative Assay of Pharmacological Agents" (U.S. patent pending 08/248,479), two embodiments of particle enhanced immunoassay are particularly preferred: a two (2-) reagent system and a three (3-) reagent system and are incorporated by reference. The embodiments are described with reference to avidin, however, other biotin-binding agents can be employed.

Generally, In the "2-reagent system", the assay is conducted using only two components: an avidin labeled particle in which all biotin binding sites have been saturated with the biotin member of a bidentate member of a biotin-analyte reagent, and an anti-analyte antibody. In the following examples, the latex-avidin particles are preincubated with the bidentate under conditions of bidentate excess, such that substantially all of the biotin binding sites are filled with the biotin member of the bidentate. After removal of the excess bidentate by size exclusion chromatography, dialysis or other means, the resulting latex-avidin analyte particle will thus be conjugated to the bidentate in a manner that permits the analyte portion of the bound bidentate to be accessible for subsequent binding with an anti-analyte antibody.

In the 3-reagent system, the assay is conducted using three components: the avidin-labeled particles, the bidentate and the anti-analyte antibody. The formation of a complex is dependent upon the binding of the latex-avidin particles to the biotin portion of the bidentate, and the binding of the anti-analyte antibody to its binding site on the analyte portion of the bidentate. Extensive complex formation is possible because both the antibody and the latex-avidin particles are capable of binding multiple bidentate molecules. For both reagent system assays, because the analyte has only a single epitope, the presence of analyte in the sample being evaluated blocks immune complex formation by competing with the bidentate for antibody binding sites. The extent of complex formation is thus inversely proportional to the concentration of analyte in the sample.

Particle enhanced bidentate assays offer several advantages as compared to the liquid formulated bidentate method. The use of particles provides better sensitivity and requires less reagent and smaller sample volumes than in the liquid based methods. The use of more diluted antibody and less sample also lowers contribution background signal. Liquid formulation bidentate technology has been described in U.S. Pat. No. 5,196,351 and has been successfully applied to assays of therapeutic drugs on both the ARRAY and Synchron.

Heparin can be included in the assay buffer and more preferably in the latex-avidin conjugate diluent. The addition of heparin to the latter can result in decreased non-specific interactions with compounds such as PEG (polyethylene glycol) present in the assay buffer.

II. INCUBATING THE REACTION MIXTURE

In the incubating step, the reaction mixture incubates for a period of time sufficient to allow formation of at least one complex. Typically, formation of large molecular complexes can be the result of a reaction between the first binding partner and the first binding member (for example, between the antibody and the drug) as well as the binding between the second binding member and the second binding partner (for example, biotin with avidin). Examples include a complex formation between the analyte of interest with assay components to detect the analyte of interest. Typically, in a bidentate conjugate inhibition of particle agglutination assay, the analyte of interest competes for the first binding partner resulting in a decrease of turbidity. This complex formation can be visualized by a change in turbidity of the reaction mixture.

III. DETECTING THE PRESENCE OF ANALYTE

In the detection of the complex formation step, the presence of the analyte in the test sample can be determined visually or with the use of an appropriate instrument. Typically, this complex formation is measured using conventional procedures such as turbidimetry, nephelometry, conventional light scattering techniques, quasielastic scattering methods or angular anisotropic scattering determination. The resulting signal given by the complex is then detected, measured and correlated to the amount of analyte from the test sample. Typically, if nephelometry or turbidity is used, the nephelometric or turbidimetric response can be measured by the rate or end-point method.

Agglutination results in increased turbidity or scatter in the reaction medium. In the presence of the analyte, agglutination of the particles occurs to an extent dependent on the amount of analyte present. In an inhibition assay, the extent of agglutination is inversely proportional to the amount of analyte present in the test sample. The amount of analyte present can be determined by using standard curves (or other standard results). This technique is well-known.

IV. TEST KIT

Formulations for use in assays to detect the analyte of interest can be assembled as test kits of at least one or more containers. These test kits can provide a convenient assortment of stable assay components which can be partially or completely pre-combined or uncombined.

In the interest of clarity, detailed examples are provided only with regard to heparin interference in avidin biotin bidentate conjugate drug assays.

In order that the present invention may be more fully understood, the following Examples and comparative results are given by way of illustration only.

EXAMPLES

The following reagents were used throughout the examples common for all experiments.

Heparin was purchased from Scientific Protein Lab (Waunakee, Wis., 170 USP units/mg). Porcine intestines were the heparin source.

Patient samples for use in correlation studies with TDx were obtained from SmithKline BioScience Lab (Van Nuys, Calif.).

Samples for heparin interference studies were prepared as follows: Human blood from Beckman employees was drawn into two or three types of Vacutainer collection tubes. One of them which contained no additives for serum samples, and the other (s), sodium or lithium heparin for heparinized plasma samples. The samples were then centrifuged, and each group of the resulting heparinized plasma and serum samples were supplemented with several levels of analyte of interest for heparin interference study. In the following Examples 1 through 10, serum and sodium heparin tubes were used for serum and plasma samples, respectively. Example 8 additionally incorporated lithium heparinized tubes.

Antibodies:

Gentamicin, phenytoin, phenobarbital, theophylline, valproic acid and carbamazepine antibodies were produced by Beckman Instruments. Acetaminophen antibody was obtained from BioDesign company.

The following examples utilized a 2-reagent system or a 3-reagent system to detect the analytes of interest. These assays are described in detail and are incorporated by reference (U.S. patent pending 08/248,479). These assays are described with reference to avidin, however, other biotin-binding reagents may be employed.

Preparation of avidin-bidentate conjugate for non-latex assays is incorporated by reference (U.S. Pat. No. 5,196, 351). Preparation of latex-avidin or latex-avidin bidentate conjugates are incorporated by reference (U.S. patent pending 08/248,479). The carboxylated modified latex particle was obtained from Seradyn, Inc. (Indianapolis, Ind.).

The initial rate method, as described in U.S. Pat. No. 5,371,021 has been used to detect and quantify serum concentration of the analytes tested, to levels as low as about 0.1 µg per mL of serum (incorporated by reference).

Quantitative results were obtained on either the Beckman Synchron CX4 or CX5 analyzer or the Beckman ARRAY 360 analyzer.

Tables 1 through 4 describe various assay formats and assay configurations which were used and will be referred to throughout Examples 1 through 10. The additional amount of heparin (40–120 units) was incorporated into the assay buffer (Examples 2 through 7) or the latex conjugate diluent (Example 8).

Two-Reagent Assay Component System

Generally, all examples utilizing the 2-reagent assay component system (with the exception of the valproic acid assay), are described according the following procedure. The two reagent assay component system features two components, the antibody as the trigger, and the latex-avidin bidentate conjugate in the latex format or the avidin bidentate in the liquid formulation. Specific amounts and timing sequence are illustrated in Tables 1–4 and are made reference to throughout the following examples.

To the assay buffer [210–230 µL, containing PBS (phosphate buffered saline), pH 7, 2.5–4.5% PEG (polyethylene glycol) was added the test sample ($\leq$3 µL, neat) and a latex avidin-bidentate conjugate [30–40 µL, containing Tris (Tris (hydroxymethyl) amino methane), pH 9, 0.2% Tween-20™ (polyoxyethylene (20) sorbitan), 0.2% bovine serum albumin for examples 1,3–4, 6–8] or an antibody (for example 2). To this reaction mixture, an antibody trigger (30–40 µL, containing PBS, pH 7, 0.2% bovine serum albumin for examples 1, 3–4, 6–8) or an avidin-bidentate conjugate trigger (for example 2) was then added and the mixture was allowed to incubate until turbidity was observed. The rate of turbidimetric response was monitored at 340 nm for 16-second cycles on a Synchron analyzer.

Three-Reagent Assay Component System

Generally, the examples utilizing the 3-reagent component system are described according to the following procedure. The three reagent assay component system features three components, the antibody, the latex-avidin particle, and the drug-biotin bidentate as the trigger. Specific amounts and timing sequences are illustrated in Tables 1-4 and are made reference to throughout the following examples.

To the assay buffer (210-230 µL, containing PBS, pH 7, 3-4% PEG with or without Triton X-100™), the test sample (≦3 µL, neat), a latex-avidin particle (30-40 µL, containing 0.02M Tris, pH 9; 0.2% Tween-20™, 0.2% BSA), and an antibody (30-40 µL, containing PBS, pH 7, 0.2% BSA were added. To this reaction mixture, a bidentate trigger (20-25 µL, containing Tris, pH 9, 0.2% Tween-20™, 0.2% BSA) was added and this mixture was allowed to incubate until turbidity was observed. The rate of turbidimetric response was monitored at 340 nm for 16-second cycles on a Synchron analyzer.

TABLE 1

GENERAL ASSAY INFORMATION

| Ex. | Analyte | Table | Detection* Method (Rate) | 2- or 3- Reagent Assay Component System | Latex Particle Size (Diameter) | No. Units Heperin[1] | Trigger |
|---|---|---|---|---|---|---|---|
| 1 | Velproic Acid | 5 | Nephelometry[3] | 2 | N/A | 0 | Antibody |
| 1 | Carbamazepine | 6 | Turbidimetry | 2 | 60 nm | 0 | Antibody |
| 2 | Gentamicin | 7 | Turbidimetry | 2 | N/A | 115 | Conjugate |
| 3 | Carbamazepine | 8 | Turbidimetry | 2 | 60 nm | 44,88 | Antibody |
| 4 | Acetaminophen | 9 | Turbidimetry | 2 | 60 nm | 44 | Antibody |
| 5 | Phenytoin | 10 | Turbidimetry | 3 | 100 nm | 44 | Bidentate |
| 7 | Phenoberbitel | 11 | Turbidimetry | 2 | 100 nm | 92 | Antibody |
| 7 | Gentemicin | 11 | Turbidimetry | 2 | 60 nm | 115 | Antibody |
| 7 | Theophylline | 11 | Turbidimetry | 2 | 60 nm | 92 | Antibody |
| 8 | Phenytoin | 12 | Turbidimetry | 2 | 60 nm | 80[2] | Antibody |

*Detection using Synchron Analyzer
[1]Heparin incorporated into the assay buffer except otherwise stated; number of units refers to amount used in reaction.
[2]Heparin included in latex-avidin-bidentate diluent; number of units refers to amount used in reaction.
[3]Detection using Array Analyzer

TABLE 2

BUFFER/REAGENT VOLUMES AND REAGENT CONFIGURATIONS

| Analyte | Table | Assay Buffer µL | Avidin- Bidentate µL | Latex- Avidin Bidentate µL | Sample µL | Antibody µL | Trigger |
|---|---|---|---|---|---|---|---|
| Valproic Acid | 5 | 600 | 42 | N/A | 42 (Diluted) | 42 | Antibody |
| Carbamazepine | 6 | 220 | N/A | 34 | 3(Neat) | 40 | Antibody |
| Gentamicin | 7 | 230 | 32 | N/A | 10(Neat) | 40 | Conjugate |
| Carbamazepine | 8 | 220 | N/A | 34 | 3(Neat) | 40 | Antibody |

TABLE 2-continued

BUFFER/REAGENT VOLUMES AND REAGENT CONFIGURATIONS

| Analyte | Table | Assay Buffer μL | Avidin-Bidentate μL | Latex-Avidin Bidentate μL | Sample μL | Antibody μL | Trigger |
|---|---|---|---|---|---|---|---|
| Acetaminophen | 9 | 220 | N/A | 32 | 3(Neat) | 40 | Antibody |
| Phenytoin[1] | 10 | 220 | N/A | N/A | 3(Neat) | N/A | Bidentate |
| Phenobarbital | 11 | 230 | N/A | 30 | 3(Neat) | 40 | Antibody |
| Gentamicin | 11 | 230 | N/A | 32 | 3(Neat) | 20 | Antibody |
| Theophylline | 11 | 230 | N/A | 40 | 3(Neat) | 30 | Antibody |
| Phenytoin | 12 | 230 | N/A | 32 | 3(Neat) | 40 | Antibody |

[1] A Latex-Avidin/Antibody Mixture was utilized.
31 μL of Latex-Avidin
31 μL of Antibody
20 μL of Bidentate The Synchron reagent cartridge has three separate compartments, two of which are separate for the assay buffer and the trigger reagent. If the assay configuration requires two or more reagents, the reagents, which are non-binding partners can be pre-mixed and transferred to the remaining available compartment (See Example 10).

TABLE 3

REAGENT ADDITIONS AND TIMING SEQUENCE ON SYNCHRON*

| Analyte | Table | Addition of Buffer & Reagent X Time = 0 Sec Reagent X = | Addition of Trigger Reagent Time = 336 Sec Trigger = | Reaction Read Window (Sec) | Reaction Read Time (Sec) |
|---|---|---|---|---|---|
| Carbamazepine | 6 | Latex-Avidin-Bidentate | Antibody | 362–386 | 24 |
| Gentamicin | 7 | Antibody | Avidin-Bidentate | 376–396 | 20 |
| Carbamazepine | 8 | Latex-Avidin-Bidentate | Antibody | 362–386 | 24 |
| Acetaminophan | 9 | Latex-Avidin-Bidentate | Antibody | 344–380 | 36 |
| Phenytoin | 10 | Latex-Avidin & Antibody | Bidentate | 344–380 | 36 |
| Phenobarbital | 11 | Latex-Avidin-Bidentate | Antibody | 355–394 | 39 |
| Gentamicin | 11 | Latex-Avidin-Bidentate | Antibody | 360–396 | 34 |
| Theophylline | 11 | Latex-Avidin-Bidentate | Antibody | 344–380 | N/A |
| Phenytoin | 12 | Latex-Avidin-Bidentate | Antibody | 336–360 | 32 |

*Sample addition time for Table 3 was Time = 320 Sec.
Table 3 shows the reagent addition and timing sequence.

After addition of the trigger reagent, measurement can begin immediately or within the first minute. Additionally, it requires less than one minute to complete the measurement by the "Initial Rate Method".

As for valproic acid (Table 1 in patent disclosure), the ARRAY instrument picks up:

600 μL Buffer

42 μL sample (diluted in buffer)

42 μL avidin-bidentate, and

42 μL antibody to start reaction

The reaction, as measured by the rate of change in light scattering, is monitored, and the maximum reaction rate is determined two minutes after the trigger reagent is added.

TABLE 4

BUFFER AND DILUENT FORMULATIONS

| Analyte | Table | Assay Buffer | Latex-Avidin or Latex-Avidin-Bidentate or Bidentate Diluent | Antiboby Diluent |
|---|---|---|---|---|
| Valproic Acid | 5 | PBS (0.02 M), 4.4% PEG, pH 7* | 0.02 M TRIS 0.2% Tween-20 ™, 0.2% BSA, pH 9* | PBS (0.02 M), 0.2% BSA, pH 7 |
| Carbamazepine | 6 | PBS (0.02 M), 4.4% PEG, pH 7* | 0.02 M TRIS, 0.2% Tween-20 ™, 0.2% BSA, pH 9* | PBS (0.02 M), 0.2% BSA, pH 7 |
| Gantamicin | 7 | PBS (0.02 M), 2.6% PEG, pH 7 500 Units Heparin/mL | 0.02 M TRIS, 0.2% Tween-20 ™, 0.2% BSA, pH 9* | PBS (0.02 M), 0.2% BSA, pH 7 |
| Carbamazepine | 8 | PBS (0.02 M), 4.4% PEG, pH 7 200 Units or 400 Units Heparin/mL | 0.02 M TRIS, 0.2% Tween-20 ™, 0.2% BSA, pH 9* | PBS (0.02 M), 0.2% BSA, pH 7 |
| Acetaminophen | 9 | PBS (0.02 M), 3.6% PEG, pH 7 200 Units Heparin/mL | 0.02 M TRIS, 0.2% Tween-20 ™, 0.2% BSA, pH 9* | PBS (0.02 M), 0.2% BSA, pH 7 |
| Phenytoin | 10 | PBS (0.02 M), 3.6% PEG, pH 7 200 Units Heparin/mL | 0.02 M TRIS, 0.2% Tween-20 ™, 0.2% BSA, pH 9* | PBS (0.02 M), 0.2% BSA, pH 7 |
| Phenobarbital | 11 | PBS (0.02 M), 3.6% PEG, pH 7 400 Units Heparin/mL | 0.02 M TRIS, 0.2% Tween-20 ™, 0.2% BSA, pH 9* | PBS (0.02 M), 0.2% BSA, pH 7 |
| Gentamicin | 11 | PBS (0.02 M), 2.9% PEG, pH 7 500 Units Heparin/mL | 0.02 M TRIS, 0.2% Tween-20 ™, 0.2% BSA, pH 9* | PBS (0.02 M), 0.2% BSA, pH 7 |
| Theophylline | 11 | PBS (0.02 M), 2.9% PEG, pH 7 400 Units Heparin/mL | 0.02 M TRIS, 0.2% Tween-20 ™, 0.2% BSA, pH 9* | PBS (0.02 M), 0.2% BSA, pH 7 |
| Phanytoin[1] | 12 | PBS (0.02 M), 3.6% PEG, pH 7* | 0.02 M TRIS, 0.2% Tween-20 ™, 0.2% BSA, pH 9 2500 Units Heparin/mL | PBS (0.02 M), 0.2% BSA, pH 7 |

*No heparin included
[1]Served as an example of incorporating heparin into the latex-avidin-bidentate conjugate diluant.

EXAMPLE 1

The Effects of Heparin Interference on Valproic Acid and Carbamazepine Assays 1. Valproic Acid Assay, Two-reagent, Liquid Formulated Test samples (plasma with valproic acid containing heparin as an interfering substance) and samples of serum free of heparin were obtained. A two-reagent assay component configuration (see Tables 1–4) was used.

The assay components included the bidentate conjugate for a liquid-formulated valproic acid bidentate conjugate assay, an assay buffer and an antibody trigger. No additional amounts of heparin were added to this assay to illustrate the effects of heparin interference using this liquid formulated valproic acid avidin bidentate conjugate assay. The results are shown in Table 5.

TABLE 5

| Sample No. | Serum µg/mL | Plasma (Heparinized) µg/mL | % Difference From Serum |
|---|---|---|---|
| 1 | 32.0 | 17.7 | −44.7 |
| 2 | 27.2 | 11.3 | −58.5 |
| 3 | 25.2 | <10 | >−60 |
| 4 | 62.4 | 39.7 | −36.4 |
| 5 | 58.5 | 43.2 | −26.2 |
| 6 | 112 | 87.2 | −22.1 |

Table 5: Serum and Heparinized Plasma VPA Concentrations in Liquid-Formulated VPA Bidentate Assay 2. Carbamazepine Assay, Two-Reagent, Latex Formulated The test samples (heparinized plasma with carbamazepine or serum free of heparin) were obtained. A two-reagent component configuration with a latex-avidin-bidentate conjugate (latex particle, 60 nm) was used (Tables 1–4). The results are shown in Table 6.

TABLE 6

| Sample No. | Serum µg/mL | Plasma (Heparinized) µg/mL |
|---|---|---|
| 1 | 13.36 | <2 |
| 2 | 13.32 | <2 |
| 3 | 14.04 | <2 |
| 4 | 13.60 | <2 |
| 5 | 13.60 | <2 |
| 6 | 8.99 | <2 |

TABLE 6-continued

| Sample No. | Serum µg/mL | Plasma (Heparinized) µg/mL |
|---|---|---|
| 7 | 9.68 | <2 |
| 8 | 9.12 | <2 |
| 9 | 9.28 | <2 |
| 10 | 9.54 | <2 |
| 11 | 4.91 | <2 |
| 12 | 3.93 | <2 |
| 13 | 9.54 | <2 |
| 14 | 8.99 | <2 |
| 15 | 9.68 | <2 |

Table 6. Serum and Heparinized Plasma Carbamazepine Concentrations in Latex-Formulated Carbamazepine Bidentate Assay on Synchron The results show that the effects due to heparin interference in plasma are lower drug concentration (compared to serum) regardless if the drug is valproic acid or carbamazepine. In addition, the results show that the effects of heparin are independent regardless of whether the assay is a liquid formulated or latex formulated.

EXAMPLE 2

Liquid-Formulated Gentamicin Bidentate Assay with Heparin in the Assay Medium

The procedure for a two-reagent component configuration was followed. Test samples of heparinized plasma with gentamicin or serum free of heparin were employed (Tables 1–4). The assay reaction mixture included 115 units of heparin (assay buffer). The results between serum and heparinized gentamicin concentrations are shown in Table 7.

TABLE 7

| Sample No. | Serum µg/mL | Plasma (Heparinized) µg/mL | % Difference From Serum |
|---|---|---|---|
| 1 | 2.87 | 2.71 | −5.5 |
| 2 | 4.40 | 5.01 | 13.9 |
| 3 | 4.78 | 5.18 | 8.4 |
| 4 | 4.33 | 5.15 | 18.9 |
| 5 | 5.29 | 5.72 | 8.1 |
| 6 | 5.35 | 5.47 | 2.2 |
| 7 | 5.35 | 5.41 | 1.1 |
| 8 | 5.03 | 5.44 | 8.2 |
| 9 | 2.84 | 2.9 | 2.1 |
| 10 | 5.30 | 5.44 | 2.6 |
| 11 | 3.03 | 3.21 | 5.9 |
| 12 | 4.88 | 5.09 | 4.3 |
| 13 | 3.03 | 3.11 | 2.6 |

TABLE 7-continued

| Sample No. | Serum µg/mL | Plasma (Heparinized) µg/mL | % Difference From Serum |
|---|---|---|---|
| 14 | 5.11 | 5.30 | 3.7 |
| 15 | 4.19 | 4.53 | 8.1 |
| 16 | 3.11 | 2.88 | −7.4 |

Table 7. Comparison of Serum and Heparinized Plasma Gentamicin Concentrations with Inclusion of 115 units of Heparin in Liquid-Formulated Gentamicin Assay on Synchron The results show that by incorporating 115 units of heparin into the assay, the differences between serum and heparinized plasma gentamicin concentrations are negligible.

EXAMPLE 3

Latex Carbamazepine Bidentate Assay with Heparin in the Assay Medium

A two-reagent component configuration was followed. 44 units of heparin were first incorporated into the assay buffer of the reaction mixture and the turbidity measured. Then, to the same samples, 88 units of heparin were added to the reaction mixture. The difference between serum and heparinized plasma carbamazepine concentrations are shown in Table 8.

TABLE 8

| | 44 Units Heparin in Assay Medium | | | 88 Units Heparin in Assay Medium | | |
|---|---|---|---|---|---|---|
| Sample No. | Serum µg/mL | Plasma (Heparinized) µg/mL | % Difference From Serum | Serum µg/mL | Plasma (Heparinized) µg/mL | % Difference From Serum |
| 1 | 5.55 | 6.91 | 24.5 | 6.58 | 6.81 | 3.5 |
| 2 | 11.57 | 11.84 | 2.3% | 12.65 | 13.12 | 3.7 |
| 3 | 15.77 | 13.33 | 15.5 | 15.65 | 16.90 | 7.9 |

Table 8. Effect of Incorporated Heparin on Serum and Heparinized Plasma Carbamazepine Samples in Latex-Based Carbamazepine Assay on Synchron The results as summarized in Table 8 indicate a difference between serum and heparinized plasma carbamazepine concentrations with 44 units of heparin added to the reaction mixture. However, by incorporating 88 units of heparin to the reaction mixture, no significant discrepancy between the serum and plasma samples were observed. Thus, in latex based carbamazepine bidentate assays, 88 units of heparin are needed to overcome the effects of heparin interference.

EXAMPLE 4

Latex Acetaminophen Bidentate Assay with Heparin in the Assay Medium

A two-reagent component configuration was followed. Test samples of heparinized plasma with acetaminophen or serum free of heparin was employed (Tables 1–4). The latex-based acetaminophen assay utilized a latex particle (60 nm). 44 units of heparin were incorporated into the assay buffer of the reaction mixture and the results of the difference between serum and heparinized plasma acetaminophen concentrations are shown in Table 9.

TABLE 9

| Sample Pool No. | Acetaminophen Spike Level | Serum | Plasma (Heparinized) µg/mL | % Difference From Serum |
|---|---|---|---|---|
| 1 | Low | 28.9 | 29.1 | 0.8 |
|   | Mid | 55.0 | 53.2 | 3.3 |
|   | High | 163.2 | 152.6 | −6.5 |
| 2 | Low | 28.4 | 28.5 | 0.6 |
|   | Mid | 55.4 | 53.8 | −2.9 |
|   | High | 157.3 | 162.8 | 3.5 |
| 3 | Low | 28.6 | 28.8 | 0.6 |
|   | Mid | 53.8 | 54.2 | 0.7 |
|   | High | 157.5 | 161.8 | 2.7 |
| 4 | Low | 28.0 | 28.1 | 0.4 |
|   | Mid | 54.8 | 55.1 | 0.6 |
|   | High | 160.50 | 159.2 | −0.9 |

Table 9. Comparison of Serum and Heparinized Plasma Acetaminophen Concentrations with Inclusion of 44 units of Heparin in Latex-Formulated Acetaminophen Assay on Synchron The results show that the difference between serum and heparinized plasma acetaminophen concentrations were negligible with the incorporation of 44 units of heparin into the assay medium and this additional amount of heparin is sufficient to mask the effects of heparin interference.

EXAMPLE 5

Latex Phenytoin Bidentate Assay with Heparin in the Assay Medium

A three-reagent assay component configuration was used (Tables 1–4). The assay components included the bidentate as the trigger reagent, the latex-avidin and the antibody for a latex-formulated phenytoin bidentate assay.

For this latex phenytoin bidentate assay, a 100 nm latex particle was used and the assay reaction mixture included 100 units of heparin (assay buffer). The results between serum and heparinized phenytoin plasma are shown in Table 10.

TABLE 10

| Sample Pool No. | Phenytoin Spike Level | Serum µg/mL | Plasma (Heparinized) µg/mL | % Difference From Serum |
|---|---|---|---|---|
| 1 | Low | 6.1 | 6.1 | −0.7 |
|   | Mid | 20.6 | 19.2 | −6.7 |
|   | High | 32.0 | 31.6 | −1.3 |
| 2 | Low | 5.9 | 5.7 | −2.6 |
|   | Mid | 18.1 | 18.8 | 3.5 |
|   | High | 29.9 | 28.4 | −5.1 |

Table 10. Comparison of Serum and Heparinized Plasma Phenytoin Concentrations with Inclusion of 44 units of Heparin in Latex-Formulated Phenytoin Assay on Synchron The results show that with the three component latex phenytoin bidentate assay, 100 units of heparin added to the reaction mixture is a sufficient amount to observe negligible differences between serum and heparinized phenytoin plasma samples.

EXAMPLE 6

Latex Acetaminophen Bidentate Assay with Heparin in the Assay Medium Three Reagent Component Assay The procedure for a three-reagent component configuration was followed. Test samples of heparinized plasma with acetaminophen and serum free of heparin were employed. The latex-based acetaminophen assay utilized a latex particle (60 nm). 44 units of heparin were incorporated into the assay buffer of the reaction mixture. In this assay, the results (not shown) indicate no significant difference between the serum and heparinized plasma samples. Furthermore, the differences between the results of the latex acetaminophen bidentate assay (two-reagent component assay), Example 4, and this three reagent component assay were negligible.

EXAMPLE 7

Latex Phenobarbital, Gentamicin and Theophylline Bidentate Assays with Heparin in the Assay Medium The procedure for a two-reagent assay component configuration was employed (Tables 1–4). Test samples of heparinized plasma with phenobarbital, heparinized plasma with gentamicin, heparinized plasma with theophylline and serum free of heparin were employed. The latex particles used were 100 nm for the phenobarbital assay, 60 nm for the gentamicin assay and 60 nm for the theophylline assay. The assay reaction mixtures included 100 units of heparin. The results of the reaction rates between serum and heparinized plasma samples of phenobarbital, gentamicin and theophylline are shown in Table 11.

TABLE 11

Comparison in Reaction Rates Between Serum and Heparinized Plasma Matrices in Latex-Based Phenobarbital, Gentamicin and Theophylline Assays on Synchron containing Approximately 100 Heparin units

| Latex-Based Assay | Heparin Units in Assay Medium | Sample No. | Reaction Rate (ΔAbs/min) Serum | Reaction Rate (ΔAbs/min) Plasma | Relative Reaction Rate (Plasma/Serum) |
|---|---|---|---|---|---|
| Phenobarbital (100 nm) | 92 | 1 | 0.20067 | 0.21246 | 105.8 |
|   |    | 2 | 0.21964 | 0.21505 | 97.9 |
|   |    | 3 | 0.21867 | 0.20855 | 95.4 |
| Gentamicin (60 nm) | 110 | 1 | 0.26438 | 0.26849 | 101.6 |
|   |    | 2 | 0.27304 | 0.27437 | 100.5 |
|   |    | 3 | 0.27813 | 0.27298 | 98.1 |
| Theophylline (60 nm) | 92 | 1 | 0.25497 | 0.25387 | 99.6 |
|   |    | 2 | 0.26577 | 0.26168 | 98.5 |
|   |    | 3 | 0.26437 | 0.25294 | 995.7 |

As mentioned, the effects of heparin interference in avidin biotin bidentate conjugate assays include increased reaction rates as compared to serum samples. The results show that for latex based two-reagent phenobarbital, gentamicin and theophylline assays, no significant differences were observed in reaction rates between serum and heparinized plasma drug samples when 100 units of heparin were introduced to the reaction mixture. Therefore, 100 units of heparin for these assays is a sufficient amount to mask the effects of heparin in the test samples.

EXAMPLE 8

Latex Phenytoin Bidentate Assays with Heparin in the Latex-Avidin Bidentate Diluent The procedure for a two-reagent component configuration was followed. Test samples of sodium and lithium heparinized plasma with phenytoin and serum free heparin were used. For this latex based assay, 80 units of heparin were included in the latex-avidin bidentate diluent. The results between serum and heparinized phenytoin plasma are shown in Table 12.

Measured absorbance background and determined rate of non-specific reaction for 2 minutes immediately after the

TABLE 12

| | | | Phenytoin Concentration | | | | | |
|---|---|---|---|---|---|---|---|---|
| | | | Plasma (Sod. Heparin) | | Plasma (Lith. Heparin) | | Plasma (EDTA) | |
| Patient Sample | Phenytoin Level | Serum µg/mL | µg/mL | % Error to Serum | µg/mL | % Error to Serum | µg/mL | % Error to Serum |
| 1 | Low  | 5.24  | 5.25  | 0.2  | 5.18  | -1.1 | 4.90  | -6.5 |
| 2 | Low  | 4.45  | 4.44  | -0.2 | 4.36  | -2.0 | 4.60  | 3.4  |
| 3 | Low  | 4.62  | 4.68  | 1.3  | 4.80  | 3.9  | 4.45  | -3.7 |
| 4 | Low  | 5.37  | 5.30  | -1.3 | 5.09  | -5.2 | 5.18  | -3.5 |
| 5 | Low  | 5.57  | 5.65  | 1.4  | 5.61  | 0.7  | 5.78  | 3.8  |
| 6 | Low  | 5.52  | 5.51  | -0.2 | 5.44  | -1.4 | 5.55  | 0.5  |
| 1 | Mid  | 13.58 | 14.12 | 4.0  | 13.08 | -3.7 | 13.13 | -3.3 |
| 2 | Mid  | 12.31 | 12.52 | 1.7  | 12.45 | 1.1  | 13.36 | 8.5  |
| 3 | Mid  | 13.69 | 13.82 | 0.9  | 13.88 | 1.4  | 13.75 | 0.4  |
| 4 | Mid  | 14.44 | 14.50 | 0.4  | 13.93 | -3.5 | 14.63 | 1.3  |
| 5 | Mid  | 16.39 | 16.32 | -0.4 | 16.69 | 1.8  | 16.31 | -0.5 |
| 6 | Mid  | 15.73 | 16.25 | 3.3  | 15.96 | 1.5  | 15.74 | 0.1  |
| 1 | High | 24.14 | 24.70 | 2.3  | 24.37 | 1.0  | 25.41 | 5.3  |
| 2 | High | 24.55 | 24.61 | 0.2  | 25.39 | 3.4  | 24.07 | -2.0 |
| 3 | High | 24.60 | 24.55 | -0.2 | 25.46 | 3.5  | 25.00 | 1.6  |
| 4 | High | 28.26 | 27.53 | -2.6 | 27.59 | -2.4 | 29.18 | 3.3  |
| 5 | High | 29.80 | 31.85 | 6.9  | 30.48 | 2.3  | 30.25 | 1.5  |
| 6 | High | 31.23 | 31.36 | 0.4  | 30.81 | -1.3 | 31.59 | 1.2  |

Comparison of Serum and Heparinized Plasma Phenytoin Concentrations with Inclusion of 80 units of Heparin in Latex-Formulated Phenytoin Assay on Synchron. (Heparin included is latex-avid-bidentate diluent.)

These results indicate no significant difference between sodium heparinized plasma samples, lithium heparinized plasma samples and serum with heparin included in the latex-avidin bidentate diluent.

EXAMPLE 9

Figure 1:
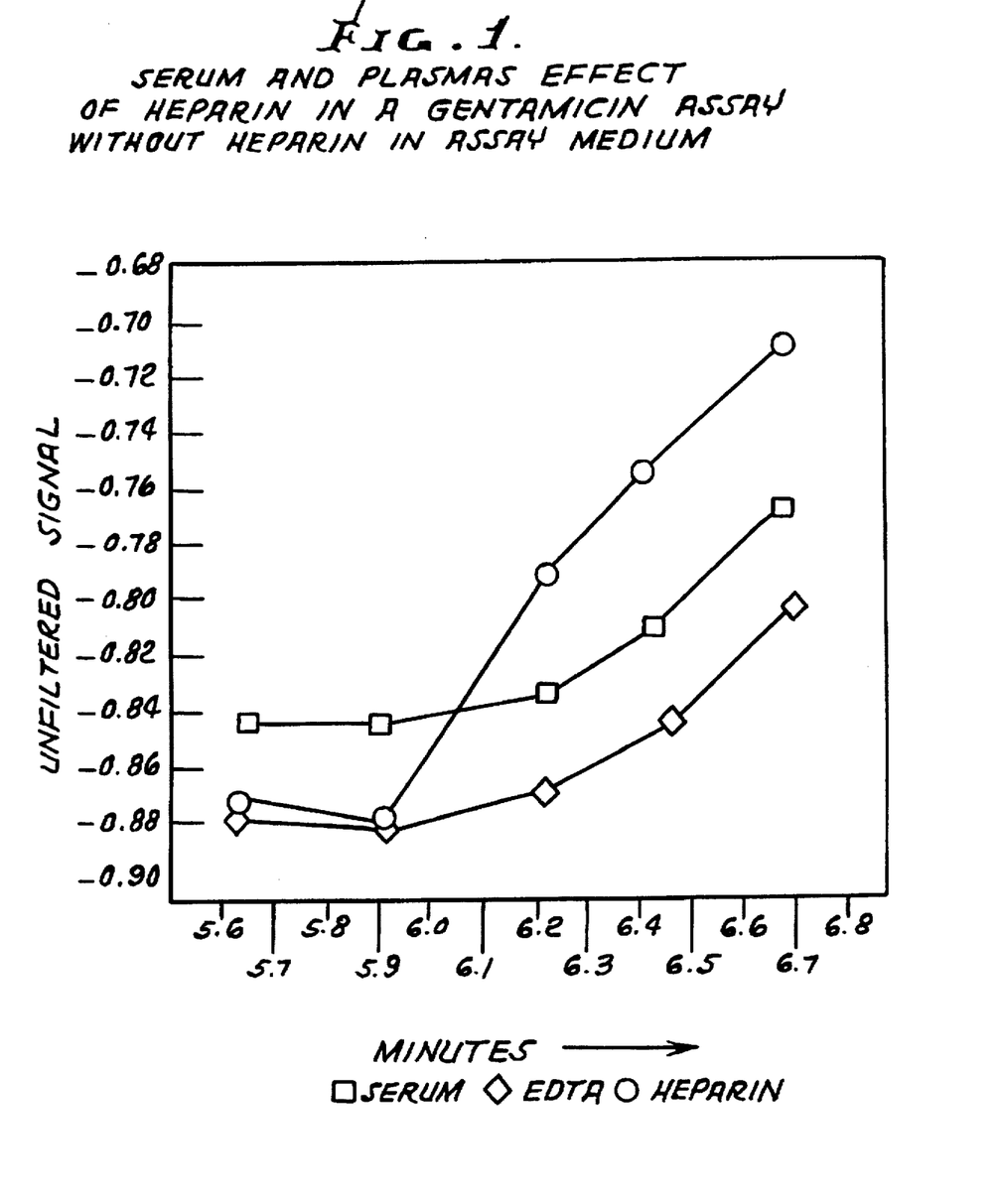
FIG. 1 is a graph showing differences in reaction profile between serum and heparinized plasma samples in a gentamicin assay.
Figure 2:
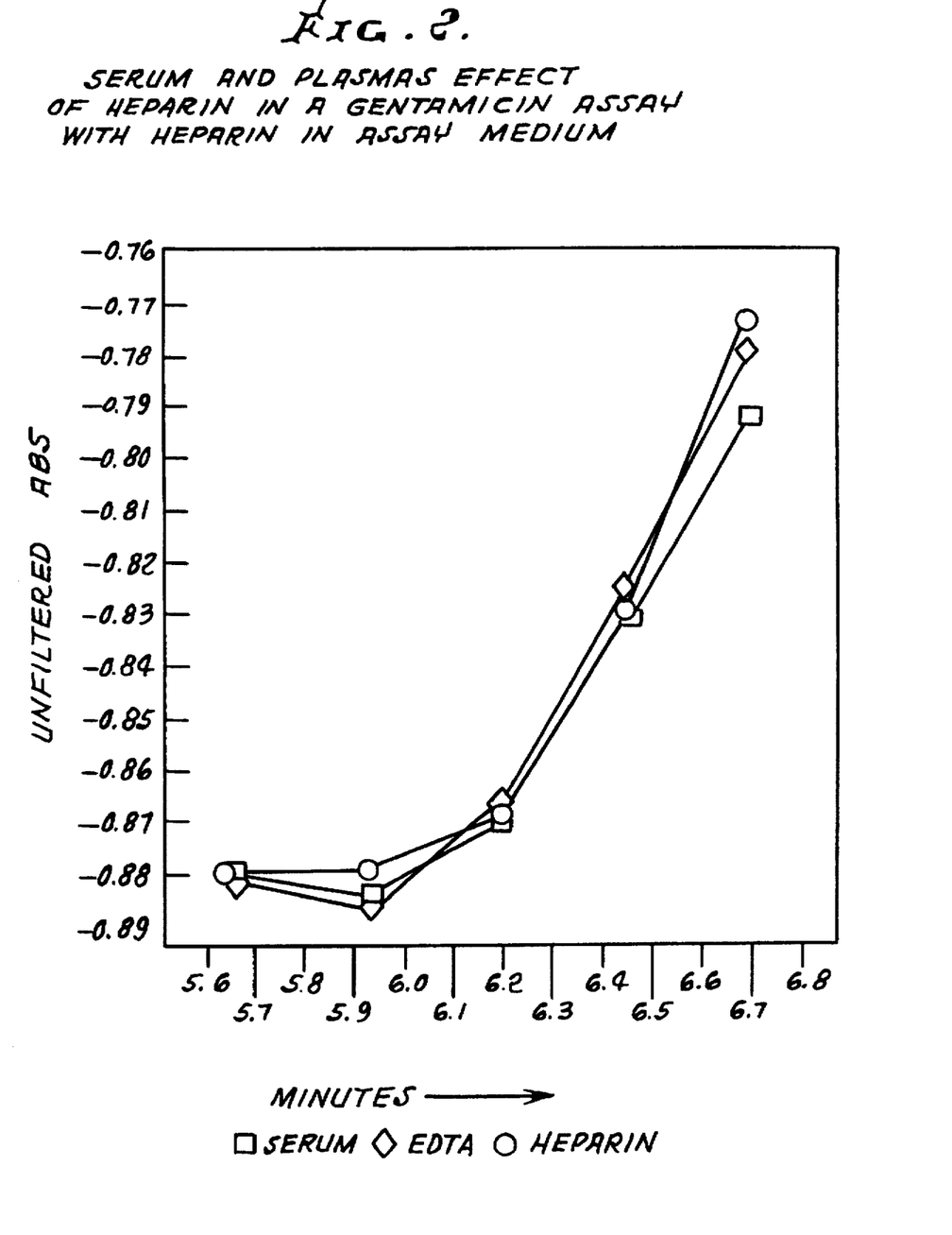
FIG. 2 is a graph showing differences in reaction profile between serum and heparinized plasma samples, with an additional amount of heparin added to the assay medium, in a gentamicin assay.

Differences in Reaction Profiles between Serum and Heparinized Plasma Samples in a Gentamicin Assay FIG. 1 illustrates the effects of heparin on serum and plasma samples in a gentamicin assay. The heparinized sample resulted in enhanced reaction rate and lower than expected recovery in concentration as compared to the corresponding serum samples. When about 60 units of heparin were added to the assay medium in an amount to mask the effects of heparin interference, no significance difference in reaction rate profile was observed (FIG. 2).

EXAMPLE 10

Advantages of Including Heparin into the Latex Conjugate Dilute as Compared to the Assay Buffer This example shows the effects of heparin interacting with PEG in the assay buffer. A two-reagent phenytoin latex avidin bidentate conjugate assay was performed. A study of the non-specific interaction between PEG (polyethylene glycol) and heparin was analyzed on a Beckman DU-70 Spectrophotometer. The reaction mixture incorporated 230× 3=690 µL of assay buffer containing PEG, Triton X-100™, heparin and sodium chloride. This was three times the volume used on the Synchron, however, the concentrations of PEG, Triton X-100™, heparin and sodium chloride remained the same. Then, 32×3µ=96 µL of latex-avidin phenytoin conjugate was added to the reaction mixture.

conjugate was introduced. Results (not shown) indicated that there was interaction between heparin and PEG and that the interaction depended on the amount of PEG used. The results also indicated that a sufficient amount of heparin (300 units/mL in assay buffer) was required to remove the non-specific reaction.

Figure 3:
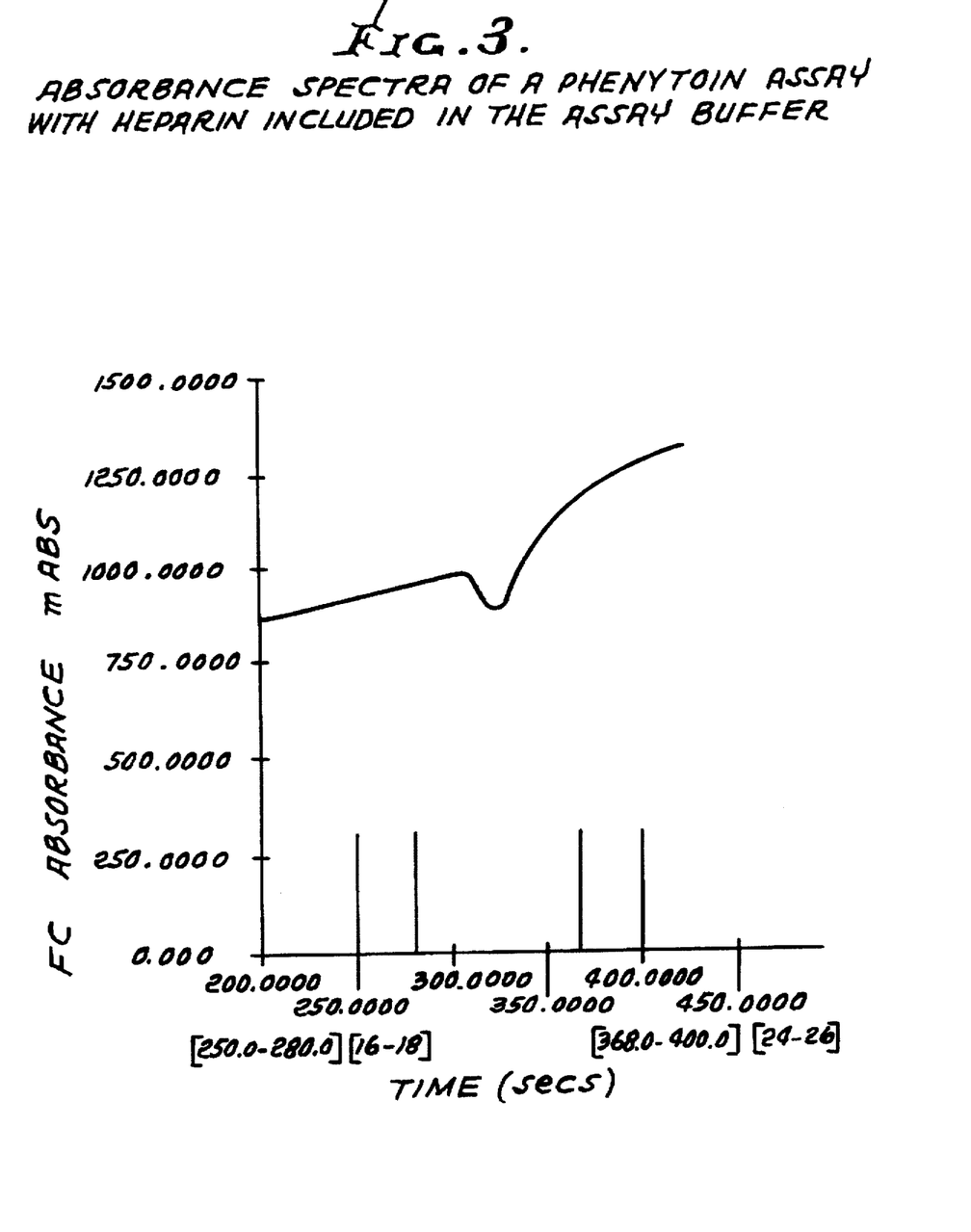
FIG. 3 is a graph showing the absorbance spectra of a phenytoin assay with heparin included in the assay buffer.
Figure 4:
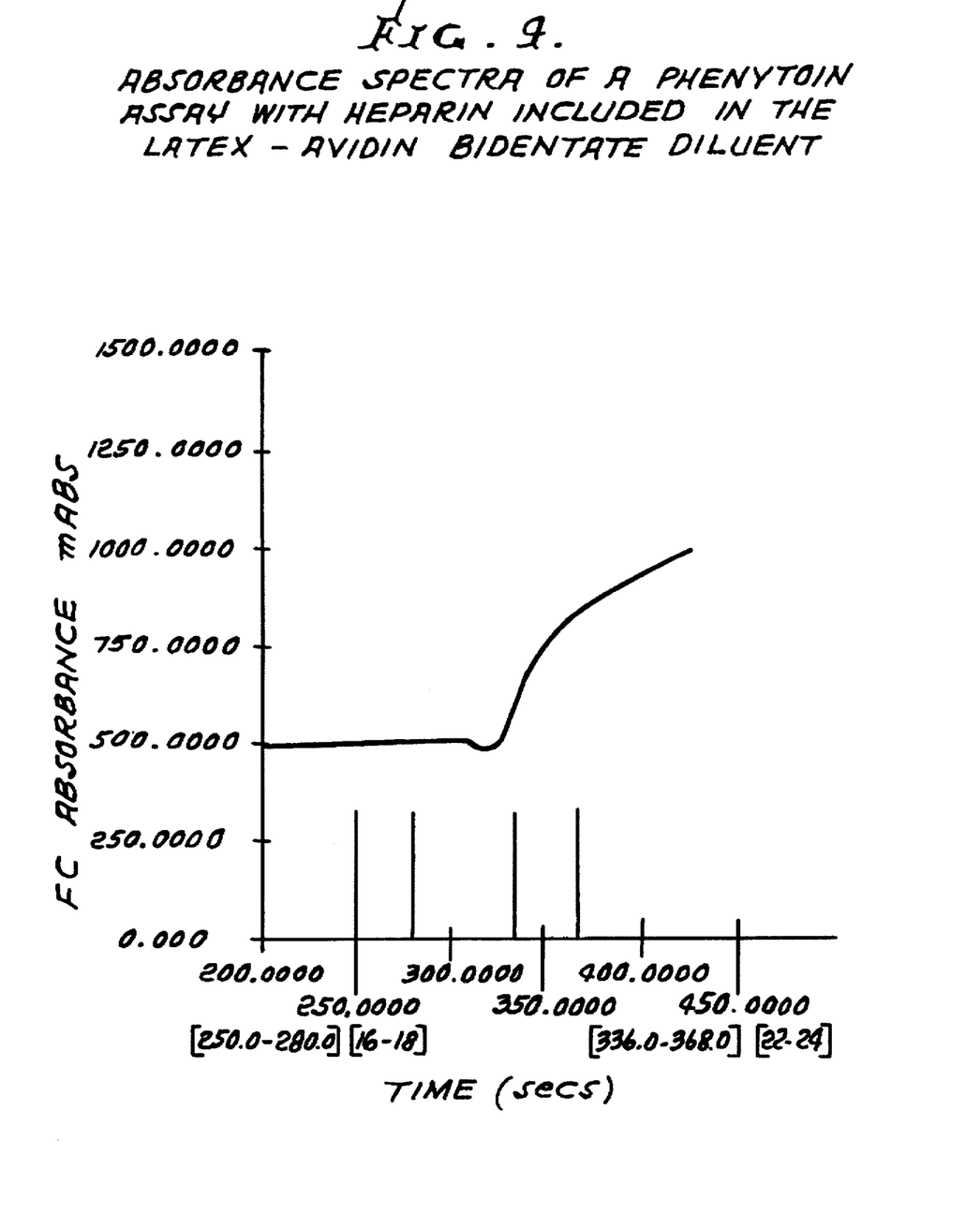
FIG. 4 is a graph showing the absorbance spectra of a phenytoin assay with heparin included in the latex-avidin bidentate diluent.

69 units of heparin was added to the assay buffer. The results are shown in FIG. 3. Another assay was performed under the same conditions described in Example 8. 80 units of heparin were included in the latex-avidin bidentate diluent. The results are shown in FIG. 4.

The results show that inclusion of heparin into the latex conjugate diluent (FIG. 4) compared to the assay buffer (FIG. 3) results in lowered background absorbance. Additionally, incorporating heparin into the latex conjugate diluent eliminated the non-specific interaction caused by the latex material and PEG before the trigger reagent was introduced. The non-specific interaction between heparin and PEG is seen by the increased slope (FIG. 3) as compared to a flatter shaped baseline (FIG. 4).

The previously described versions of the present invention have many advantages. The advantages include having an assay which can detect an analyte of interest in a test sample with little or no effects from an interfering substance (i) without rigorous pre-treatment of the test sample and (ii) without the addition of new factors which could interfere with the assay. According to this invention, by adding an interfering substance which is already present in the test sample, sample variation is reduced and the sensitivity and accuracy of the assay is maintained.

Although the present invention has been described in considerable detail with reference to certain preferred versions, other versions are possible. Thus the spirit and scope of the appended claims should not be limited to the description of the preferred versions contained herein.

What is claimed is:

1. An assay for detecting the presence of an analyte of rest in a test sample comprising the steps of:
   a. forming a reaction mixture by combining in au assay medium:
      (i) an assay system comprising a first binding member, a second binding member, a spacer member intermediate between the members, a first binding partner and a second binding partner, the first binding member capable of binding to the first binding partner, the first binding partner capable of binding to the analyte, the second binding member capable of binding to the second binding partner, the second binding partner aiding detection of either bound or unbound analyte in the reaction mixture;
      (ii) a test sample containing the analyte and heparin as an interfering substance that is capable of interfering with the assay by interacting with the second binding partner, and
      (iii) an additional mount of the heparin in a quantity effective to substantially mask the effect of the interfering substance in the test sample, and wherein the additional amount of heparin is in an effective quantity such that substantially all of the second binding partners in the reaction mixture are non-specifically bound to the interfering substance heparin;
   b. incubating the reaction mixture undex conditions sufficient to allow the formation of a complex between the analyte and the first binding partner; and
   c. determining the presence of the analyte in the test sample by measuring the extent of any formation of the complex, the extent being proportional to the concentration of the analyte in the sample.

2. The assay of claim 1, wherein the first and second binding members are members of a bidentate compound.

3. The assay of claim 1, wherein the first binding member is selected, from the group consisting of theophylline, carbamazepine, gentamicin, acetaminophen, phenytoin, and phenobarbital.

4. The assay of claim 2, wherein the second binding member is biotin.

5. The assay of claim 2, wherein the second binding partner is avidin.

6. The assay of claim 5, wherein the avidin is conjugated to latex.

7. The assay of claim 1, wherein the first binding partner which specifically binds to the analyte of interest is an antibody or an antibody fragment.

8. The assay of claim 1, wherein the assay system further comprises a third binding member, the third binding member capable of being attached to the spacer intermediate.

9. The assay of claim 8, wherein the first, second and third binding members are members of a tridentate compound.

10. The assay of claim 1, wherein the additional amount of heparin added to the reaction mixture is from about 20 units to about 150 units.

11. The assay of claim 1, wherein the additional amount of heparin added to the reaction mixture is from about 40 units to about 120 units.

12. The assay of claim 1, wherein the additional amount of heparin added to the reaction mixture is from about 40 units to about 90 units.

13. The assay of claim 1, wherein the test sample is selected from the group consisting of serum, plasma, saliva, cerebral spinal fluid, amniotic fluid, urine, feces, mucus, cell extracts, tissue extracts, and pus.

14. The assay of claim 1, wherein the analyte of interest is selected from the group consisting of drugs, hormones, vitamins, enzymes, proteins, antibodies, polysaccharides, bacteria, protozoa, parasites, fungi, viruses, cell antigens, tissue antigens, blood cell substances, and blood fluid substances.

15. The assay of claim 14, wherein the analyte of interest is a drug.

16. The assay of claim 15, wherein the drug is selected from the group consisting of theophylline, carbamazepine, gentamicin, acetaminophen, phenytoin, phenobarbital, digoxin, valproic acid, thyroxine, disopyramide, lidocaine, procainamide, propranolol, guanidine, amikacin, chloramphenicol, kanamycin, tobramycin, tricyclic antidepressants, ethosuximide, primidone, acetylsalicylic acid, and methotrexate.

17. An assay for detecting the presence of an analyte of interest in a test sample comprising the steps of:
   forming a reaction mixture by combining in an assay medium:
      (I) an assay system comprising a first binding member, a second binding member, a spacer member intermediate between the members, a first binding partner and a second binding partner, the first binding member capable of binding to the first binding partner, the first binding partner capable of binding to the analyte, the second binding member capable of binding to the second binding partner, the second binding partner aiding detection of either bound or unbound analyte in the reaction mixture;
      (ii) a test sample containing the analyte and heparin as an interfering substance that is capable of interfering with the assay by interacting with the second binding partner, and
      (iii) an additional mount of the heparin in a quantity effective to substantially mask the effect of the interfering substance in the test sample, wherein the additional amount of heparin is between about 40 units to about 90 units, and wherein the additional amount of heparin is in an effective quantity such that substantially all of the second binding partners in the reaction mixture are non-specifically bound to the interfering substance heparin:
   b. incubating the reaction mixture under conditions sufficient to allow the formation of a complex between the analyte and the first binding partner, and
   c. determining the presence of the analyte in the test sample by measuring the extent of any formation of the complex, the extent being proportional to the concentration of the analyte in the sample.

18. A test kit for detecting the presence of an analyte of interest in a test sample, the test sample containing an interfering substance that is capable of interfering with the assay, the test kit comprising at least one container containing the following components which can be partially or completely pre-combined or uncombined;
   a. an assay medium;
   b. a first binding member capable of binding to a first binding partner for the analyte;
   c. the first binding partner capable of binding to the analyte;
   d. a second binding member capable of binding to a second binding partner;
   e. the second binding partner aiding detection of either bound or unbound analyte in the reaction mixture, wherein the interfering substance in the test sample is heparin and is capable of interfering with the assay by interacting with the second binding partner, and f. an additional amount of heparin in a quantity effective to substantially mask the effect of the interfering substance in the test sample and wherein the additional amount of heparin is in an effective quantity such that substantially all of the second binding partners in the reaction mixture are non-specifically bound to the interfering substance heparin.

19. The test kit of claim 18, wherein the additional amount of heparin added is from about 20 units to about 150 units.

20. The test kit of claim 18, wherein the additional amount of heparin added to the reaction mixture is from about 40 units to about 120 units.

21. The test kit of claim 18, wherein the additional amount of heparin added to the reaction mixture is from about 40 units to about 90 units.

22. The test kit of claim 18, wherein the test sample is selected from the group consisting of serum, plasma, saliva, cerebral spinal fluid, amniotic fluid, urine, feces, mucus, cell extracts, tissue extracts, and pus.

23. The test kit of claim 18, wherein the analyte of interest is selected from the group consisting of drugs, hormones, vitamins, enzymes, proteins, antibodies, polysaccharides, bacteria, protozoa, parasites, fungi, viruses, cell antigens, tissue antigens, blood cell substances, and blood fluid substances.

24. The test kit of claim 23, wherein the analyte of interest is a drug.

25. The test kit of claim 24, wherein the drug is selected from the group consisting of theophylline, carbamazepine, gentamicin, acetaminophen, phenytoin, phenobarbital, digoxin, valproic acid, thyroxine, disopyramide, lidocaine, procainamide, propranolol, guanidine, amikacin, chloramphenicol, kanamycin, tobramycin, tricyclic antidepressants, ethosuximide, primidone, acetylsalicylic acid, and methotrexate.

26. The assay of claim 1, wherein the additional amount of the interfering substance heparin is first added to the assay system.

27. The assay of claim 17, wherein the additional amount of the interfering substance heparin first added to the assay system.

28. The assay of claim 18, wherein the additional amount of the interfering substance heparin is first added to the assay system.

* * * * *

UNITED STATES PATENT AND TRADEMARK OFFICE
CERTIFICATE OF CORRECTION

PATENT NO.    : 5,705,353
DATED         : January 6, 1998
INVENTOR(S)   : Oh et al.

It is certified that error appears in the above-identified patent and that said Letters Patent is hereby corrected as shown below:

Column 21,
Line 2, remove "rest" and insert -- interest --.
Line 4, remove "au" and insert -- an --.

Signed and Sealed this

Eleventh Day of February, 2003

JAMES E. ROGAN
*Director of the United States Patent and Trademark Office*